(12) United States Patent
Ogura (10) Patent No.: US 10,634,635 B2
(45) Date of Patent: Apr. 28, 2020

(54) DIELECTRIC CONSTANT MICROSCOPE AND METHOD OF OBSERVING ORGANIC SPECIMEN

(71) Applicant: National Institute of Advanced Industrial Science and Technology, Chiyoda-ku, Tokyo (JP)

(72) Inventor: Toshihiko Ogura, Tsukuba (JP)

(*) Notice: Subject to any disclaimer, the term of this patent is extended or adjusted under 35 U.S.C. 154(b) by 96 days.

(21) Appl. No.: 16/082,895

(22) PCT Filed: Mar. 7, 2017

(86) PCT No.: PCT/JP2017/009103
§ 371 (c)(1),
(2) Date: Sep. 6, 2018

(87) PCT Pub. No.: WO2017/154936
PCT Pub. Date: Sep. 14, 2017

(65) Prior Publication Data
US 2019/0049399 A1    Feb. 14, 2019

(30) Foreign Application Priority Data

Mar. 9, 2016  (JP) .................................. 2016-045990

(51) Int. Cl.
| G01R 27/26 | (2006.01) |
| G01N 27/22 | (2006.01) |
| G01N 33/483 | (2006.01) |
| G01N 33/48 | (2006.01) |
| G02B 21/06 | (2006.01) |
| G02B 21/34 | (2006.01) |

(52) U.S. Cl.
CPC .......... *G01N 27/221* (2013.01); *G01N 33/48* (2013.01); *G01N 33/4833* (2013.01);
(Continued)

(58) Field of Classification Search
CPC ... G01N 27/221; G01N 33/4833; G01N 33/48
See application file for complete search history.

(56) References Cited

U.S. PATENT DOCUMENTS

2004/0207396 A1* 10/2004 Xiao ...................... G01Q 10/04
324/244
2013/0003521 A1   1/2013 Tran et al.
(Continued)

FOREIGN PATENT DOCUMENTS

| JP | 2002-286617 | 10/2002 |
| JP | 2013-108871 | 6/2013 |
| JP | 2013-134952 | 7/2013 |
| JP | 2014-203733 | 10/2014 |

OTHER PUBLICATIONS

International Search Report dated Apr. 4, 2017 for PCT/JP2017/009103.
(Continued)

*Primary Examiner* — Thang X Le
*Assistant Examiner* — Alvaro E Fortich
(74) *Attorney, Agent, or Firm* — Soei Patent & Law Firm (57) ABSTRACT

A dielectric constant microscope to observe a shape of a micro organic specimen includes first and second insulating films that are disposed to oppose each other such that the organic specimen along with the solution is interposed therebetween, and application-side conductive films P1 to Pn (where n is an integer greater than 1). The application-side conductive films are separated from each other on an outward surface of the first insulating film. Additionally, the dielectric constant microscope includes measurement-side conductive films p1 to pm (where m is an integer greater than 1) that are separated from each other on an outward surface of the second insulating film. Input signals Sf1 to Sfn having potential change at different frequencies are applied to the application-side conductive films P1 to Pn, potential change is measured for each of the measurement-side conductive films p1 to pm, and the organic specimen is visualized from a dielectric constant distribution between the
(Continued)

first and second insulating films obtained by separating the potential change depending on the frequencies.

20 Claims, 7 Drawing Sheets

(52) U.S. Cl.
CPC ......... *G01R 27/2641* (2013.01); *G02B 21/06* (2013.01); *G02B 21/34* (2013.01)

(56) References Cited

U.S. PATENT DOCUMENTS

2016/0025659 A1* 1/2016 Ominami ................ H01J 37/20
250/307
2017/0010456 A1* 1/2017 Gopinath ........... G02B 21/0032

OTHER PUBLICATIONS

T.Ogura, "Direct Observation of Unstained Biological Specimens in Water by the Frequency Transmission Electric-Field Method Using SEM", PLoS One vol. 9, 2014, p. 1-p. 6.
T.Ogura, "Nanoscale analysis of unstained biological specimens in water without radiation damage using high-resolution frequency transmission electric-field system based on FE-SEM", Biochemical and Biophysical Research Communications, 2015, p. 521-p. 528.
International Preliminary Report on Patentability with Written Opinion dated Sep. 11, 2018 for PCT/JP2017/009103.

* cited by examiner

Fig.7

DIELECTRIC CONSTANT MICROSCOPE AND METHOD OF OBSERVING ORGANIC SPECIMEN

CROSS-REFERENCE TO RELATED APPLICATIONS

This application is a 35 U.S.C. § 371 national phase application of PCT/JP2017/009103, filed Mar. 7, 2017, which is based upon and claims the benefit of priority from Japanese Patent Application No. 2016-045990, filed Mar. 9, 2016.

TECHNICAL FIELD

The invention relates to a microscope that observes a specimen including an organism such as a biological specimen and an observation method thereof, and more particularly, to a dielectric constant microscope that visualizes an organic specimen by measuring a dielectric constant distribution and a method of observing an organic specimen.

BACKGROUND ART

Observation of a micro organic specimen including a biological specimen such as bacteria or virus or a biological tissue which has been cut out from a part of a living thing requires the use of a scanning electron microscope. However, with a scanning electron microscope, there are several problems in observing an organic specimen in that an electron beam cannot be applied to a specimen which has not been maintained in vacuum of a predetermined level or higher and the specimen is likely to be damaged by the applied electron beam. In order to solve these problems, an observation method of fixing an organic specimen using paraformaldehyde or the like and coating the surface of the specimen with a conductive material such as gold, platinum, or carbon to protect the surface, an observation method of dyeing a specimen with a heavy metal, and the like have been employed. On the other hand, an observation method for acquiring a high-contrast image of an organic specimen using an electron beam without performing pretreatment on the specimen has been proposed.

For example, Patent Literature 1 discloses a method of observing an internal structure of an organic specimen by detecting a spatial distribution of electrons (tunneling electrons) passing through the organic specimen in a scanning electron microscope. An organic specimen is attached to a conductive film of a stacked body of an insulating film and a conductive film and the insulating film is irradiated with an electron beam from an electron gun. At this time, secondary electrons generated in the insulating film form a large potential gradient in the stacked body and are discharged to the conductive film due to a tunneling effect. These electrons also pass through the organic specimen by tunneling and an image reflecting the internal structure of the organic specimen is obtained by detecting the passing electrons using a secondary electron detector. Since an organic specimen is not directly irradiated with an electron beam from an electron gun and thus damage to the specimen is small, the pretreatment on the organic specimen can be skipped.

Non Patent Literature 1 describes a method of observing an organic specimen in a scanning electron microscope with the organic specimen immersed in an aqueous solution. When a metal film is formed on an insulating film and is then irradiated with an electron beam, local potential change is caused and an attenuation state when the electron beam passes through the organic specimen in the aqueous solution can be observed as an image (a changing potential transmission observation method). Such a method employs the following phenomenon. That is, since the specific dielectric constant of water is about 80 which is large, water is not affected by the potential change and transmits the electron beam. Since the specific dielectric constant of an organic specimen ranges from about 2 to 3 which is small, the organic specimen is greatly affected by the potential change and attenuates the electron beam. Because an organic specimen is not directly irradiated with an electron beam from an electron gun, the organic specimen does not have to be disposed in a vacuum, and pretreatment on the organic specimen can be skipped.

Similarly, Patent Literature 2 discloses a method of observing an organic specimen which is maintained in an aqueous solution in a scanning electron microscope. Specifically, an organic specimen is interposed with an aqueous solution between a pair of insulating films opposing each other, a conductive film formed on an outward surface of one insulating film is scanned and irradiated with an electron beam while the intensity thereof is changed in a pulse shape, and potential change on an outward surface of the other insulating film is detected. When a part of the conductive film on which an electron beam is incident has a negative charge, electric dipoles of water molecules in the aqueous solution are arranged in accordance with a potential gradient, but this state is released by blocking the electron beam. When ON/OFF of an electron beam is repeated at a frequency of 1 kHz or higher and signals of the same frequency components are extracted by the detection side, potential change can be separated with a high resolution. By narrowing an irradiation diameter of an electron beam to about 1 nm, a resolution of 1 nm at the same level is obtained.

CITATION LIST

Patent Literature

Patent Literature 1: Japanese Unexamined Patent Publication No. 2013-134952
Patent Literature 2: Japanese Unexamined Patent Publication No. 2014-203733

Non Patent Literature

Non Patent Literature 1: T. Ogura, "Direct observation of unstained biological specimens in water by the frequency transmission electric-field method using SEM," PLOS ONE Vol. 9, e92780(6 pp) (2014)

SUMMARY OF INVENTION

Technical Problem

There is demand for observing a shape of an organic specimen. For example, in a method of observing an organic specimen maintained in an aqueous solution, since a large dielectric constant gap is caused in an interface between an organic specimen and an aqueous solution, a shape of an organic specimen can be observed by electrically measuring the spatial arrangement of such a gap.

The invention is made in consideration of the above-mentioned circumstances and an objective thereof is to provide a dielectric constant microscope that can observe a shape of a micro organic specimen and an observation method thereof.

Solution to Problem

A dielectric constant microscope according to the invention is a dielectric constant microscope for visualizing an organic specimen in a solution, the dielectric constant microscope including: first and second insulating films disposed to oppose each other such that the organic specimen is interposed therebetween with the solution; application-side conductive films $P_1$ to $P_n$ (where n is an integer greater than 1) disposed to be regularly separated from each other on an outward surface of the first insulating film; and measurement-side conductive films $p_1$ to $p_m$ (where in is an integer greater than 1) that are disposed to be regularly separated from each other on an outward surface of the second insulating film, wherein input signals $S_{f1}$ to $S_{fn}$, having potential change at different frequencies are applied to the application-side conductive films $P_1$ to $P_n$, potential change is measured for each of the measurement-side conductive films $p_1$ to $p_m$, and the organic specimen is visualized from a dielectric constant distribution between the first and second insulating films obtained by separating the potential change depending on the frequencies.

According to the invention, since spatial change of a dielectric constant in the solution due to insertion of an organic specimen can be measured by dielectric constant change measurement pairs based on a plurality of combinations of application-side conductive films and measurement-side conductive films, it is possible to observe a shape of the organic specimen. Since a plurality of dielectric constant change measurement pairs can be measured in a short time, it is possible to clearly visualize the organic specimen, for example, even when the specimen changes in a short time.

In the invention, at least one of a combination of the first insulating film and the application-side conductive films or a combination of the second insulating film and the measurement-side conductive films may be formed of a transparent material, and an optical microscope that is able to observe the organic specimen from the one combination side may be provided. According to the invention, since the organic specimen can be observed by additionally using the optical microscope, it is possible to easily check a specimen position or the like.

In the invention, the dielectric constant distribution may be acquired to correspond to each of the lines connecting the application-side conductive films $P_1$ to $P_n$ and the measurement-side conductive films $p_1$ to $p_m$. According to the invention, it is possible to acquire a dielectric constant distribution corresponding to the shape of the organic specimen between the insulating films from the dielectric constant change for each of the lines connecting the application-side conductive films and the measurement-side conductive films.

In the invention, each of the application-side conductive films $P_1$ to $P_n$ may include a first penetration electrode that penetrates the first insulating film and is exposed from the opposing surface thereof. In the invention, each of the measurement-side conductive films $p_1$ to $p_m$ may include a second penetration electrode that penetrates the second insulating film and is exposed from the opposing surface thereof. According to the invention, it is possible to enhance an electromagnetic interaction between the application-side conductive films and/or the measurement-side conductive films and the solution and thus to improve a resolution of an acquired image.

A method of observing an organic specimen according to the invention is a method of observing an organic specimen using a dielectric constant microscope for visualizing the organic specimen in a solution, the dielectric constant microscope including: first and second insulating films that are disposed to oppose each other; application-side conductive films $P_1$ to $P_n$ (where n is an integer greater than 1) that are disposed to be regularly separated from each other on an outward surface of the first insulating film; measurement-side conductive films $p_1$ to $p_m$ (where m is an integer greater than 1) that are disposed to be regularly separated from each other on an outward surface of the second insulating film, the method including: interposing the organic specimen with the solution between the first and second insulating films; and applying input signals $S_{f1}$ to $S_{fn}$ having potential change at different frequencies to the application-side conductive films $P_1$ to $P_n$, measuring potential change for each of the measurement-side conductive films $p_1$ to $p_m$, and visualizing the organic specimen from a dielectric constant distribution between the first and second insulating films obtained by separating the potential change depending on the frequencies.

According to the invention, since spatial change of a dielectric constant in the solution due to insertion of an organic specimen can be measured by dielectric constant change measurement pairs based on a plurality of combinations of application-side conductive films and measurement-side conductive films, it is possible to observe a shape of the organic specimen. Since a plurality of dielectric constant change measurement pairs can be measured in a short time, it is possible to clearly visualize the organic specimen, for example, even when the specimen changes in a short time.

In the invention, a dielectric constant ratio for each of the lines connecting the application-side conductive films $P_1$ to $P_n$, and the measurement-side conductive films $p_1$ to $p_m$ may be calculated from an output voltage variation in each of the measurement-side conductive films $p_1$ to $p_m$ corresponding to an input voltage variation of a maximum voltage and a minimum voltage for each of the input signals $S_{f1}$ to $S_{fn}$. According to the invention, it is possible to acquire a dielectric constant distribution corresponding to the shape of the organic specimen between the insulating films from the dielectric constant change for each of the lines connecting the application-side conductive films and the measurement-side conductive films.

DESCRIPTION OF EMBODIMENTS

The inventor of the invention has investigated obtaining images visualizing a three-dimensional shape of a micro organic specimen such as bacteria or a virus. When a specimen (a dielectric) having a dielectric constant different from that of the surroundings is inserted between a pair of electrodes opposing each other, electromagnetic change corresponding to a change of the dielectric constant is measured between the electrodes. When a plurality of electrode pairs are arranged with a specimen therebetween, a two-dimensional image of an object is obtained. By arranging a plurality of dielectric constant change measurement pairs while spatially changing their directions (angles), a three-dimensional image such as a stereoscopic photograph is obtained.

Hereinafter, a dielectric constant microscope according to an embodiment of the invention will be described with reference to FIGS. 1 to 4.

Figure 1:
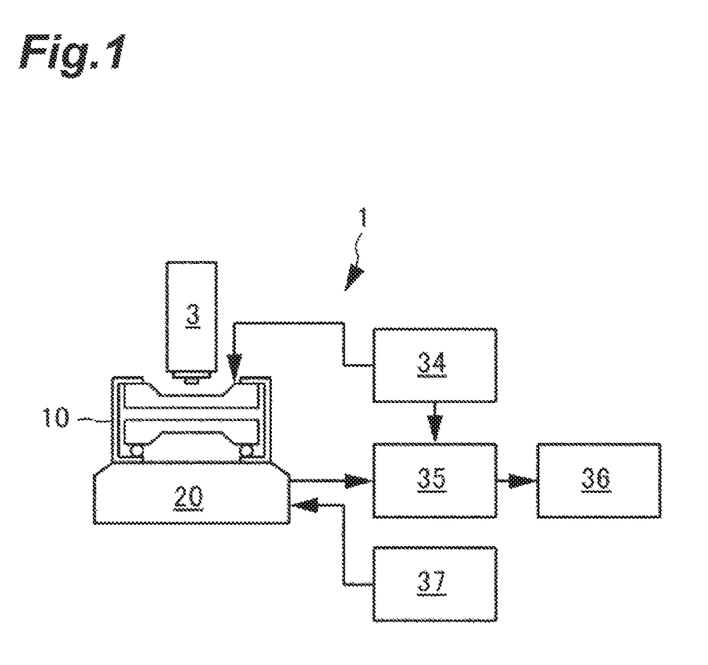
FIG. 1 is a block diagram of a dielectric constant microscope according to the invention.

As illustrated in FIG. 1, a dielectric constant microscope 1 is a device that includes a stage 20 and an observation holder 10 detachably installed thereon and that observes an organic specimen 18 in the observation holder 10. Examples of the organic specimen 18 include a biological specimen such as bacteria or a virus and a biological specimen which has been cut out from a part of a living thing.

Figure 2:
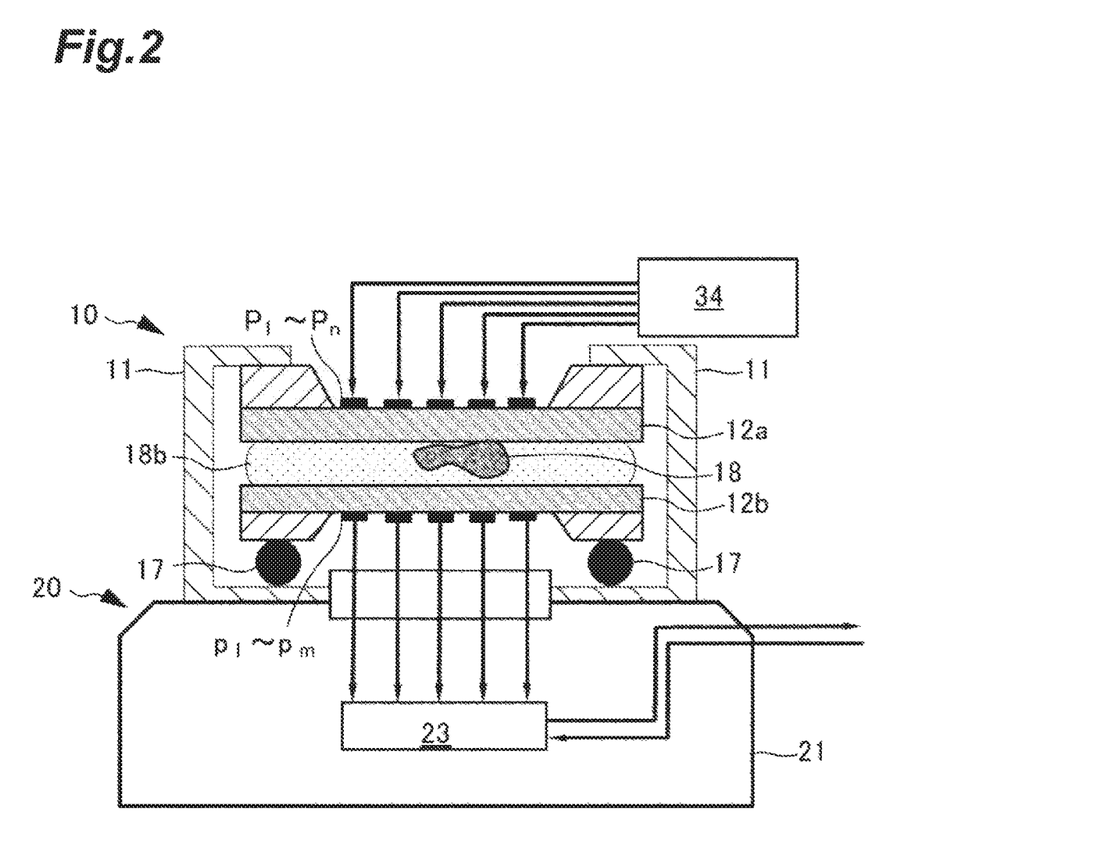
FIG. 2 is a sectional view of a main part of the dielectric constant microscope according to the invention.

Referring additionally to FIG. 2, the observation holder 10 includes an external frame 11 that includes a window on the top and the bottom thereof and insulating films 12a and 12b that close the top window and the bottom window from the inside. The insulating film 12a that closes the top window maintains an aqueous solution 18b including the organic specimen 18 on the bottom surface thereof from the top side, and a plurality of application-side electrodes $P_1$ to $P_n$ formed of a conductive film are stacked on the top surface thereof. The electrodes $P_1$ to $P_n$ are arranged to be regularly separated from each other on the insulating film 12a. Here, n is an integer greater than 1 (equal to or greater than 2).

The insulating film 12b that closes the bottom window maintains the aqueous solution 18b including the organic specimen 18 on the top surface thereof from the bottom side, and a plurality of measurement-side electrodes $p_1$ to $p_m$ formed of a conductive film are stacked on the bottom surface thereof. The electrodes $p_1$ to $p_m$ are arranged to be regularly separated from each other on the insulating film 12b. Here, m is an integer greater than 1 (equal to or greater than 2).

That is, the insulating films 12a and 12b are disposed to oppose each other in parallel such that the organic specimen 18 and the aqueous solution 18b are interposed therebetween. Here, for example, it is preferable that the thickness of the insulating films 12a and 12b be equal to or less than 100 nm. The insulating films 12a and 12b come into contact with the inner surface of the observation holder 10 using an O ring 17, a packing which is not illustrated, a spacer, or the like, and the gap therebetween is maintained at a predetermined dimension equal to or less than 50 μm.

Figure 3:
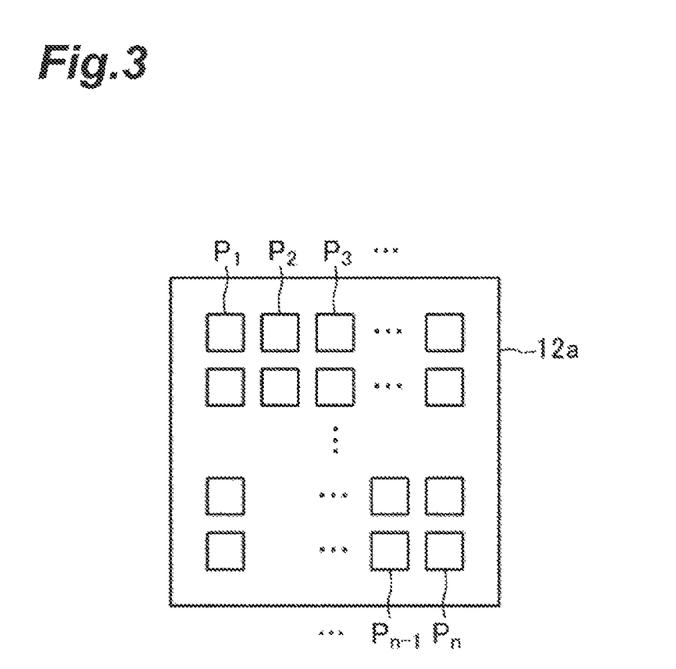
FIG. 3 is a top view of a main part of the dielectric constant microscope according to the invention.

Referring additionally to FIG. 3, for example, it is preferable that the application-side electrodes $P_1$ to $P_n$ be arranged to be equally spaced longitudinally and laterally on the insulating film 12a. It is also preferable that the measurement-side electrodes $p_1$ to $p_m$ be arranged in the same way as the application-side electrodes. The positions of the electrodes on the insulating film 12a or 12b have only to be regularly determined and, for example, another regular arrangement may be employed in which the electrodes are densely arranged in the vicinity of the center thereof and the electrodes are widely spaced in the periphery thereof. The application-side electrodes and the measurement-side electrodes may be arranged differently from each other.

Since a resolution of an acquired image can be improved as the size of the electrodes and the interval therebetween in a direction along the principal surfaces of the insulating films 12a and 12b decrease, it is preferable that intervals at which the electrodes are arranged be set to several μm or less. For example, when the electrode size and the interval are determined such that the electrodes are parallel to each other at intervals of 100 nm, a shape of the organic specimen 18 can be observed up to two times the interval, that is, 200 nm. This is equivalent to the resolution of an optical microscope and the electrode size may be set to achieve a resolution smaller than that.

Figure 4:
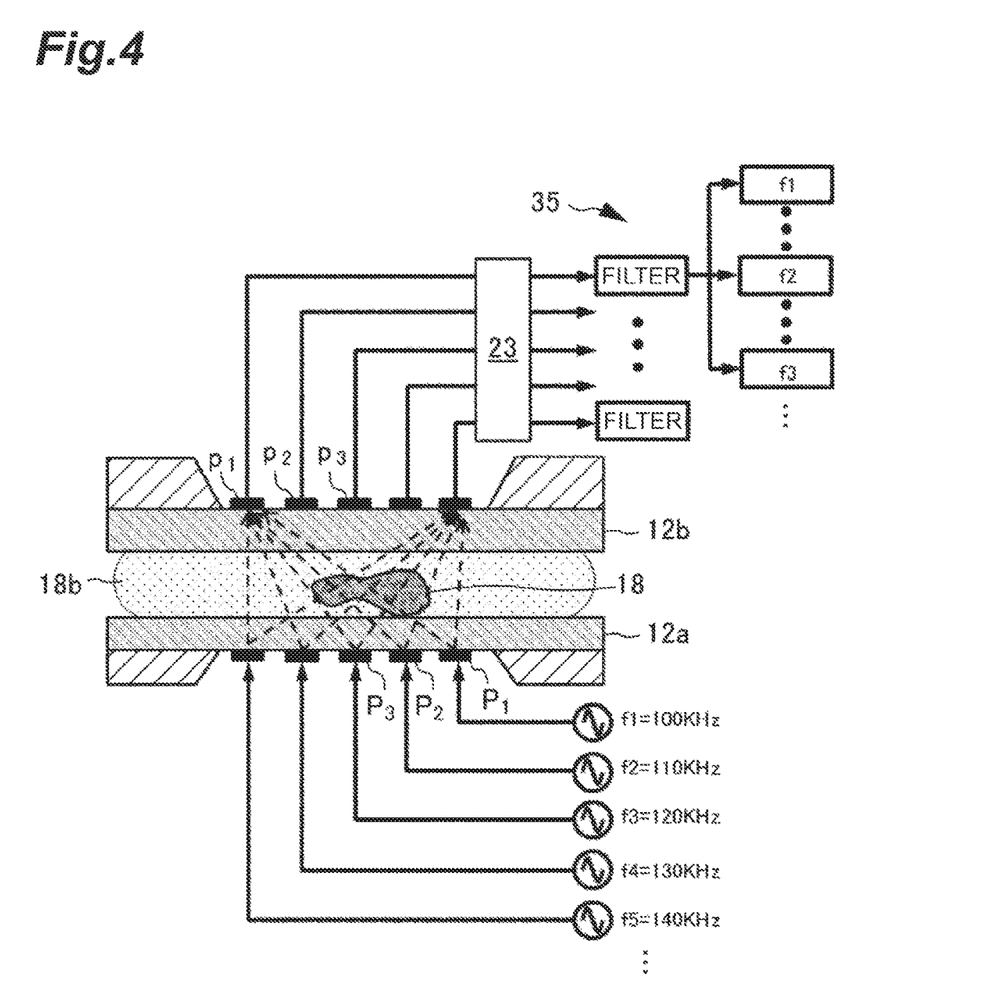
FIG. 4 is a sectional view of a main part of the dielectric constant microscope illustrating an example of an observation method according to the invention.

Referring additionally to FIG. 4, the application-side electrodes $P_1$ to $P_n$ are connected to a voltage controller 34, and input signals $S_{f1}$ to $S_{fn}$ that change in potential at different frequencies f1 to fn are individually applied thereto. The measurement-side electrodes $p_1$ to $p_m$ are connected to an amplifier 23, and signals based on individual potential change of the measurement-side electrodes $p_1$ to $p_m$ based on the input signals $S_{f1}$ to $S_{fn}$ applied to the application-side electrodes $P_1$ to $P_n$ can be amplified. In FIG. 2, the upper side is defined as an application side and the lower side is defined as a measurement side, but the insulating films 12a and 12b are interchangeable with each other such that the application electrodes are disposed on the bottom side and the measurement-side electrodes are disposed on the top side, as illustrated in FIG. 4.

The stage 20 includes a casing 21 and has the amplifier 23 built therein. The amplifier 23 sends an amplified signal to a signal separator 35. The signal separator 35 receives a reference signal for the potential change of the input signals $S_{f1}$ to $S_{fn}$ applied from the voltage controller 34, separates a received signal into signals corresponding to the application-side electrodes $P_1$ to $P_n$ on the basis of the frequencies f1 to fn, and outputs the separated signals to a shape analyzer 36. Although details will be described later, the shape analyzer 36 measures the potential change of the measurement-side electrodes $p_1$ to $p_n$, calculates dielectric constants between the measurement-side conductive films $p_1$ to $p_n$ and the application-side electrodes $P_1$ to $P_n$, and generates an image for the organic specimen 18 on the basis thereof. A power supply 37 for operation of the built-in amplifier 23 or the like is connected to the stage 20.

It is preferable that the dielectric constant microscope 1 additionally include an optical microscope 3 that can observe the organic specimen 18. In this case, the insulating film and the electrodes (conductive films) on the optical microscope 3 side are formed of a transparent conductive material. Accordingly, the optical microscope may be used to align the observation position of the organic specimen 18 by comparing an image of the organic specimen 18 acquired by the dielectric constant microscope 1 with an image from the optical microscope. In this embodiment, the optical microscope 3 is disposed above the observation holder 10 to face downward, but may be disposed in the casing 21, that is, below the observation holder 10, to face upward.

A method of observing the organic specimen 18 using the dielectric constant microscope 1 will be described below with reference to FIGS. 1, 2, and 4.

First, as illustrated in FIG. 2, the organic specimen 18 is maintained in the observation holder 10 with the aqueous solution 18b and is set on the stage 20.

Subsequently, as illustrated in FIG. 4, input signals $S_{f1}$ to $S_{fn}$ that change in potential at different frequencies f1 to fn are individually applied to the application-side electrodes $P_1$ to $P_n$. Here, input signals of n types of different frequencies that change to increase from 100 kHz by 10 kHz are applied.

In the drawing, the application-side electrodes are disposed on the lower side and the measurement-side electrodes are disposed on the upper side.

For example, when an input signal $S_{f1}$ is applied to the application-side electrode $P_1$, potential change corresponding to the dielectric constants of the organic specimen 18 and the aqueous solution 18b interposed therebetween is given to the measurement-side electrode $p_1$. Similarly, potential change corresponding to the dielectric constants of the organic specimen 18 and the aqueous solution 18b interposed therebetween is given to the measurement-side electrode $p_1$ by the input signals $S_{f2}$ to $S_{fn}$ applied to the application-side electrodes $P_2$ to $P_n$, and potential change in which the potential changes are superimposed is caused as a result.

Referring additionally to FIG. 1, the potential change of the measurement-side electrode $p_1$ is amplified as a signal by the amplifier 23 built in the stage 20 and is sent to the signal separator 35. The signal separator 35 separates the received signal based on the potential change of the measurement-side electrode $p_1$ in frequency. That is, the signal separator 35 separates the received signal based on the potential change on the measurement side into n types of signals at the n types of frequencies f1 to fn by causing the signal to pass through a band pass filter or the like on the basis of a reference signal from the voltage controller 34. That is, the potential change of the measurement-side electrode $p_1$ based on the dielectric constants between the application-side electrodes $P_1$ to $P_n$ and the measurement-side electrode $p_1$ can be separated and obtained. The potential change separated at the frequencies f1 to fn is output to the shape analyzer 36. The same is true of the other measurement-side electrodes $p_2$ to $p_m$.

The shape analyzer 36 can calculate the dielectric constants on lines connecting the application-side electrodes $P_1$ to $P_n$ and the measurement-side electrodes $p_1$ to $p_m$ from the signals based on the potential change from the measurement-side electrodes $p_1$ to $p_m$. That is, the separated signal of the measurement-side electrode $p_1$ corresponding to the application-side electrode $P_1$ is a signal of the frequency f1, and varies in voltage in proportion to the dielectric constant between the electrodes on the basis of a voltage variation of a maximum voltage and a minimum voltage of the electrode $P_1$ due to the input signal $S_{f1}$ applied to the application-side electrode $P_1$. That is, the shape analyzer 36 can calculate the dielectric constant between the measurement-side electrode $p_1$ and the application-side electrode $P_1$ from the voltage variation of the separated potential change. Here, the dielectric constant can be acquired as a dielectric constant ratio to a dielectric constant when only the aqueous solution 18b is interposed therebetween.

Accordingly, for example, a dielectric constant distribution viewed from the measurement-side electrode $p_1$ can be acquired as a two-dimensional image. The two-dimensional image is an oblique image in which images directed to the application-side electrodes $P_1$ to $P_n$, that is, directed to the lines having different oblique angles when viewed from the measurement-side electrode $p_1$, are continuous. The same is true of the other measurement-side electrodes $p_2$ to $p_m$ and the same oblique image may be acquired for the application-side electrodes $P_1$ to $P_n$.

Here, since the organic specimen 18 such as a biological specimen has a much smaller dielectric constant than the aqueous solution 18b, the dielectric constant greatly varies depending on a distance between the electrodes in the lines occupied by the organic specimen 18. That is, in the oblique image, the two-dimensional shape of the organic specimen 18 is visualized into an image on the basis of the dielectric constant distribution. Since the oblique image is acquired on the basis of the dielectric constants of the lines connecting the electrodes and intersecting each other, the shape analyzer 36 can reconstruct the oblique image depending on the positions and angles of the lines to obtain a three-dimensional image of the organic specimen 18. That is, a position of the organic specimen 18 at which the dielectric constant in a certain line varies is determined from the dielectric constants of the other intersecting lines and a three-dimensional image is acquired. This is the same principle as acquiring a three-dimensional image, for example, by combining two-dimensional images in different directions like a stereoscopic image.

As described above, according to this embodiment, the organic specimen 18 can be stereoscopically visualized from the dielectric constant distribution between the insulating films 12a and 12b. Particularly, it is possible to easily observe a three-dimensional image without performing dyeing treatment or fixing treatment on the organic specimen 18 in the aqueous solution 18b. The organic specimen 18 is subjected to potential change, and thus, for example, a biological specimen can be observed in a living state. Since measurement can be performed for a short time, it is possible to clearly visualize a specimen, for example, when the specimen changes for a short time. For example, without using a large-scaled device such as an electron gun or a vacuum device in an electron microscope, it is possible to observe a specimen under the atmospheric pressure.

The input signals $S_{f1}$ to $S_{fn}$ which are applied to the application-side electrodes $P_1$ to $P_n$ are not particularly limited as long as signals based on the individual potential change of the measurement-side electrodes $p_1$ to $p_m$ are only separated to correspond to the input signals $S_{f1}$ to $S_{fn}$. That is, an input signal with potential change at one frequency can be applied to the electrodes as described above, and an input signal with potential change in which a plurality of frequencies are superimposed may be applied to one electrode. This will be described below with reference to FIGS. 5 and 6.

Figure 5:
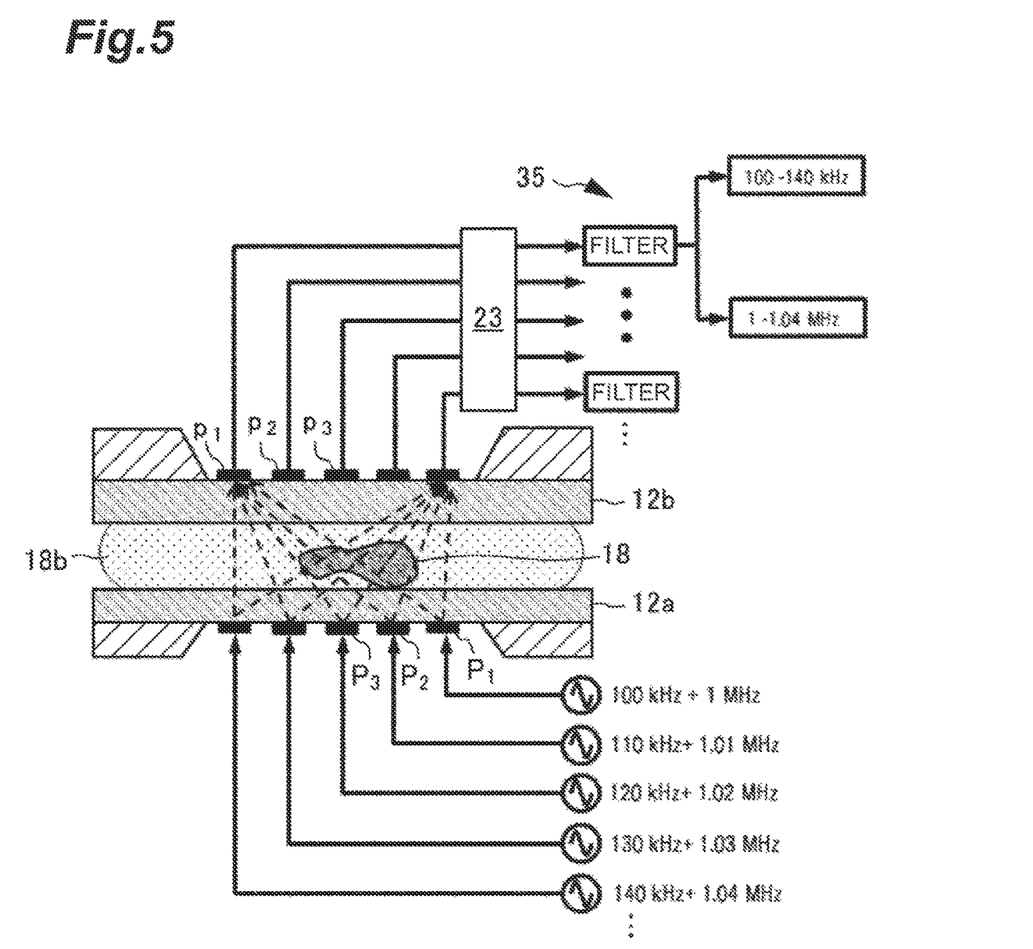
FIG. 5 is a sectional view of a main part of the dielectric constant microscope illustrating another example of the observation method according to the invention.

For example, as illustrated in FIG. 5, input signals $S_{f1}'$ to $S_{fn}'$ which are applied to the application-side electrodes $P_1$ to $P_n$ may be based on potential change obtained by superimposing potential change at n types of frequencies which increase from 100 kHz by 10 kHz as described and potential change at frequencies obtained by adding 900 kHz to the frequencies for each electrode. That is, for example, an input signal $S_{f1}'$ based on potential change in which potential change at 100 kHz and potential change at 1,000 kHz (1 MHz) are superimposed is applied to the application-side electrode $P_1$. The signal separator 35 can separate the signal based on potential change of the measurement-side electrode, for example, to correspond to the frequencies of 100 kHz and 1 MHz. That is, the shape analyzer 36 (see FIG. 1) can acquire oblique images based on two high and low frequencies for each combination of one measurement-side electrode and one application-side electrode. Three-dimensional shapes based on two high and low frequencies can be obtained and visualized as images. By obtaining such oblique images or a three-dimensional image from a plurality of types of frequencies, it is possible to obtain a three-dimensional shape of the organic specimen 18 and also to analyze a three-dimensional structure or a material composition of the organic specimen 18.

Figure 6:
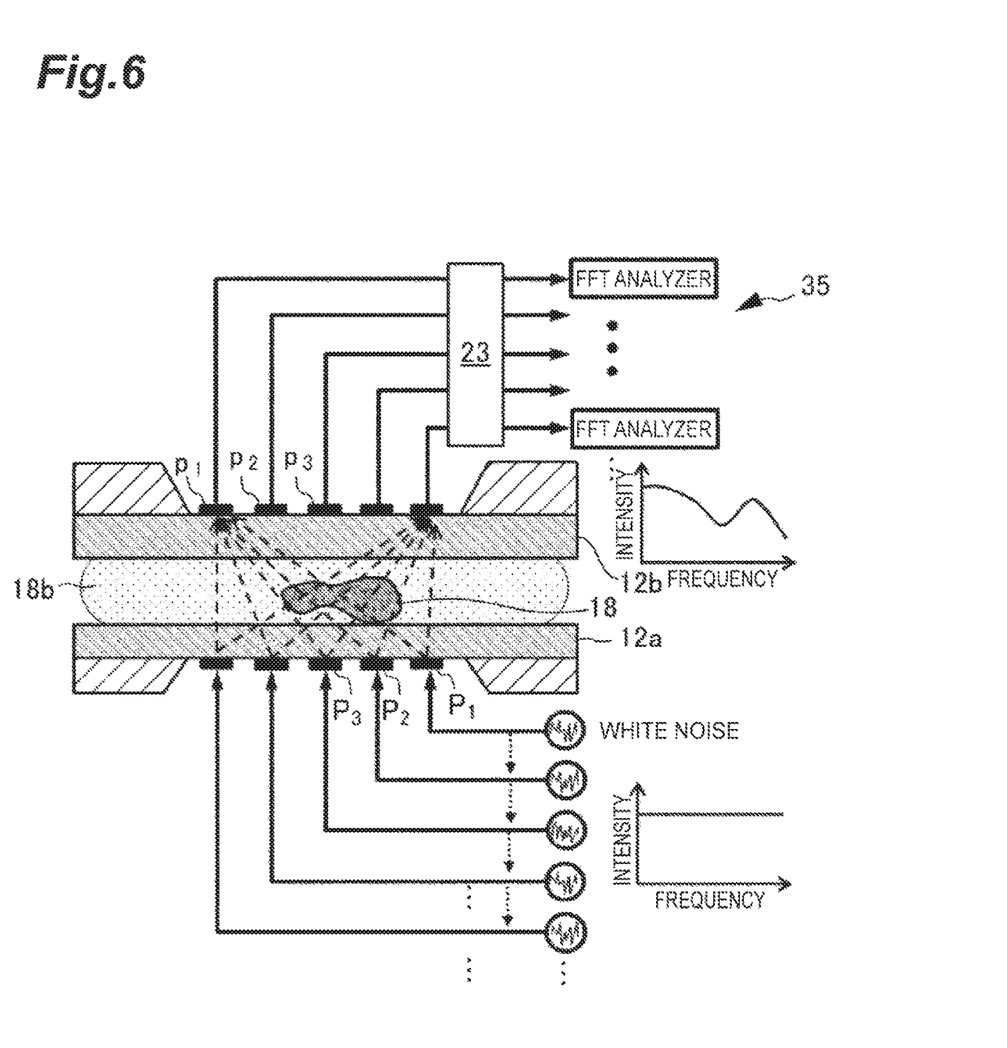
FIG. 6 is a sectional view of a main part of the dielectric constant microscope illustrating another example of the observation method according to the invention.

As illustrated in FIG. 6, the input signals S which are applied to the application-side electrodes $P_1$ to $P_n$ may be set to the same signal. For example, potential change including so-called white noise in which the same intensity is obtained at all frequencies when a frequency spectrum is acquired by Fourier transform is applied as the input signal S to the electrodes sequentially, that is, at different times. The signal separator 35 can separate the received signal depending on the application times to the application-side electrodes and thus it is possible to distinguish which of the application-side electrodes $P_1$ to $P_n$ the separated signals correspond to. The signal separator 35 acquires intensity change for each frequency of the received signal using an FFT analyzer. That is, a frequency spectrum is obtained by performing frequency-decomposition the received signal using the fast Fourier transform. Accordingly, the shape analyzer 36 (see FIG. 1) can obtain an oblique image at an arbitrary frequency or a three-dimensional image and obtain a three-dimensional shape of the organic specimen 18, and it is also possible to more specifically analyze a three-dimensional structure or a material composition of the organic specimen 18.

A modified example of a structure of an electrode will be described below with reference to FIG. 7.

Figure 7:
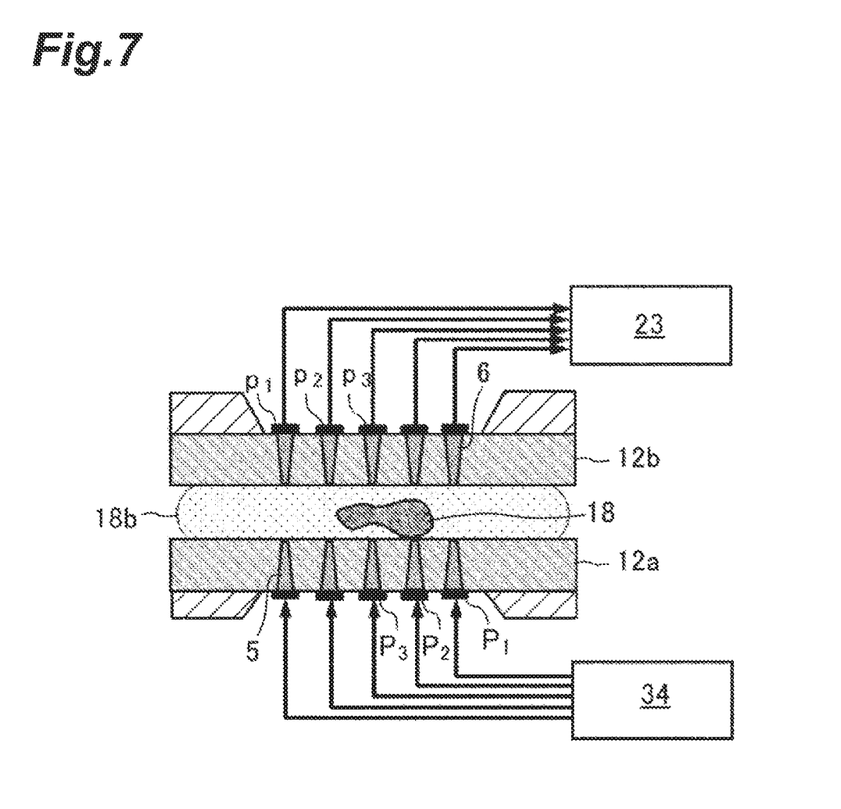
FIG. 7 is a sectional view of a main part of a dielectric constant microscope according to another embodiment.

As illustrated in FIG. 7, each of the application-side electrodes $P_1$ to $P_n$ may be connected to a penetration electrode 5 that penetrates the insulating film 12a and is exposed from the surface on the side on which the organic specimen 18 is held. Accordingly, each of the electrodes $P_1$ to $P_n$ approaches the corresponding measurement-side electrodes $p_1$ to $p_m$ and thus it is possible to improve a resolution of an acquired image. It is preferable that the penetration electrode 5 have a tip sharpened toward the surface on the side on which the organic specimen 18 is held. Accordingly, it is possible to enhance an electromagnetic interaction between the application-side electrodes $P_1$ to $P_n$ and the solution, and to improve a resolution of an acquired image.

Similarly, each of the measurement-side electrodes $p_1$ to $p_m$ may be connected to a penetration electrode 6 that penetrates the insulating film 12b and is exposed from the surface on the side on which the organic specimen 18 is held. It is preferable that the penetration electrode 6 have a tip sharpened toward the surface on the side on which the organic specimen 18 is held. Accordingly, it is also possible to improve a resolution of an acquired image as described above.

While embodiments of the invention and modified examples based thereon have been described above, the invention is not limited thereto and those skilled in the art will be able to find out various substitutions and modifications without departing from the gist of the invention or the scope of the appended claims.

REFERENCE SIGNS LIST

1 Dielectric constant microscope
3 Optical microscope
10 Observation holder
12a Insulating film
12b Insulating film
18 Organic specimen
18b Aqueous solution
$P_1$ to $P_n$ Electrodes (application-side)
$p_1$ to $p_m$ Electrodes (measurement-side)

The invention claimed is:

1. A dielectric constant microscope for visualizing an organic specimen in a solution, the dielectric constant microscope comprising:
first and second insulating films disposed to oppose each other such that the organic specimen is interposed therebetween with the solution;
application-side conductive films $P_1$ to $P_n$ (where n is an integer greater than 1) that are separated from each other on an outward surface of the first insulating film; and
measurement-side conductive films $p_1$ to $p_m$ (where m is an integer greater than 1) that are separated from each other on an outward surface of the second insulating film,
wherein input signals $S_{f1}$ to $S_{fn}$ having potential change at different frequencies are applied to the application-side conductive films $P_1$ to $P_m$ the potential change is measured for each of the measurement-side conductive films $p_1$ to $p_m$, and the organic specimen is visualized from a dielectric constant distribution between the first and second insulating films obtained by separating the potential change depending on the different frequencies.

2. The dielectric constant microscope according to claim 1, wherein a combination selected from a group of combinations including a first combination of the first insulating film and the application-side conductive films $P_1$ to $P_n$ and a second combination of the second insulating film and the measurement-side conductive films $p_1$ to $p_m$ is formed of a transparent material, and
an optical microscope configured to observe the organic specimen from a side of the dielectric constant microscope comprising the selected combination formed of the transparent material.

3. The dielectric constant microscope according to claim 1, wherein the dielectric constant distribution is acquired to correspond to each electrode pair combination between the application-side conductive films $P_1$ to $P_n$ and the measurement-side conductive films $p_1$ to $p_m$.

4. The dielectric constant microscope according to claim 1, wherein each of the application-side conductive films $P_1$ to $P_n$ includes a first penetration electrode that penetrates the first insulating film and is exposed from the opposing surface thereof.

5. The dielectric constant microscope according to claim 1, wherein each of the measurement-side conductive films $p_1$ to $p_m$ includes a second penetration electrode that penetrates the second insulating film and is exposed from the opposing surface thereof.

6. A method of observing an organic specimen using a dielectric constant microscope for visualizing the organic specimen in a solution, the dielectric constant microscope including: first and second insulating films that oppose each other; application-side conductive films $P_1$ to $P_n$ (where n is an integer greater than 1) that are separated from each other on an outward surface of the first insulating film; and measurement-side conductive films $p_1$ to $p_m$ (where m is an integer greater than 1) that are separated from each other on an outward surface of the second insulating film, the method comprising:
interposing the organic specimen between the first and second insulating films with the solution;
applying input signals $S_{f1}$ to $S_{fn}$ having potential change at different frequencies to the application-side conductive films $P_1$ to $P_n$;
measuring the potential change for each of the measurement-side conductive films $p_1$ to $p_m$; and
visualizing the organic specimen from a dielectric constant distribution between the first and second insulating films obtained by separating the potential change depending on the different frequencies.

7. The method of observing an organic specimen according to claim 6, wherein a dielectric constant ratio for each electrode pair combination between the application-side conductive films $P_1$ to $P_n$ and the measurement-side conductive films $p_1$ to $p_m$ is calculated from an output voltage variation in each of the measurement-side conductive films $p_1$ to $p_m$ corresponding to an input voltage variation of a maximum voltage and a minimum voltage for each of the input signals $S_{f1}$ to $S_{fn}$.

8. The method of observing an organic specimen according to claim 6, further comprising:
amplifying a plurality of measurement-side signals having the potential change measured at the measurement-side conductive films $p_1$ to $p_m$;
separating the measurement-side signals; and
outputting the separated measurement-side signals to a shape analyzer.

9. The method of observing an organic specimen according to claim 8, further comprising:
receiving a reference signal for the potential change of the input signals $S_{f1}$ to $S_{fn}$, wherein the measurement-side signals are separated on the basis of the frequencies f1 to fn of the reference signal.

10. The method of observing an organic specimen according to claim 6, further comprising:
calculating dielectric constants between the measurement-side conductive films $p_1$ to $p_n$ and the application-side conductive films $P_1$ to $P_n$; and
generating an image for the organic specimen based on the calculated dielectric constants.

11. The method of observing an organic specimen according to claim 10, wherein the dielectric constants are calculated based on the potential change from the measurement-side conductive films $p_1$ to $p_m$, and wherein the potential change from the measurement-side conductive films $p_1$ to $p_m$ vary in voltage in proportion to the dielectric constants.

12. The method of observing an organic specimen according to claim 6, further comprising:
acquiring a dielectric constant distribution viewed from the measurement-side conductive films $p_1$ to $p_m$ as a plurality of continuous two-dimensional oblique images directed to the application-side conductive films $P_1$ to $P_n$.

13. The method of observing an organic specimen according to claim 6, wherein the input signals $S_{f1}$ to $S_{fn}$ vary in frequency by increments of 10 kHz.

14. The dielectric constant microscope according to claim 1, wherein the first and second insulating films are parallel to each other.

15. The dielectric constant microscope according to claim 1, wherein a thickness associated with each of the first and second insulating films is 100 mm or less.

16. The dielectric constant microscope according to claim 1, wherein the first and second insulating films contact an inner surface of an observation holder using one or more O rings.

17. The dielectric constant microscope according to claim 1, wherein the application-side conductive films $P_1$ to $P_n$ are equally spaced longitudinally and laterally on the first insulating film.

18. The dielectric constant microscope according to claim 17, wherein the measurement-side conductive films $p_1$ to $p_m$ are equally spaced longitudinally and laterally on the second insulating film.

19. The dielectric constant microscope according to claim 1, wherein one of the first and second insulating films is formed of a transparent conductive material.

20. The dielectric constant microscope according to claim 1, wherein the application-side conductive films $P_1$ to $P_n$ or the measurement-side conductive films $p_1$ to $p_m$ are formed of a transparent material.

* * * * *